US00PP17088P3

(12) United States Plant Patent
Krüger

(10) Patent No.: US PP17,088 P3
(45) Date of Patent: Sep. 12, 2006

(54) POINSETTIA PLANT NAMED 'FISCOR ELECTRIC'

(50) Latin Name: *Euphorbia pulcherrima*
Varietal Denomination: Fiscor Electric

(75) Inventor: Dirk Krüger, Gärtnersiedlung 4, 24610 Gönnebek (DE)

(73) Assignee: Dirk Krüger, Gönnebek (DE)

( * ) Notice: Subject to any disclaimer, the term of this patent is extended or adjusted under 35 U.S.C. 154(b) by 182 days.

(21) Appl. No.: 10/932,073

(22) Filed: Sep. 2, 2004

(65) Prior Publication Data

US 2006/0048255 P1 Mar. 2, 2006

(51) Int. Cl.
*A01H 5/00* (2006.01)

(52) U.S. Cl. ..... Plt./307
(58) Field of Classification Search ..... Plt./307, Plt./303
See application file for complete search history.

(56) References Cited

PUBLICATIONS

UPOV–ROM GTITM, Plant Variety Database, 2005/01, GTI Jouve Retrieval Software. Citation for *Rosa* 'Fiscor Electric'.*

Official Gazette of the Community Plant Variety Office, 2004. Citation for *Euphorbia* 'Fiscor Electric', Grant No. 13660.*

Switzerland application and denomination No. 161, Jan. 2004. Citation for *Euphorbia* 'Fiscor Electric', application No. 03–2070.*

Switzerland grant No. 166, Nov. 30, 2004. Citation for *Euphorbia* 'Fiscor Electric', grant No. 04.1710.*

Germany—Application No. EUP 231, filed Dec. 24, 2001, Denomination Form dated Sep. 15, 2003, and Withdrawn Form dated Jun. 15, 2004, confirming application withdrawn date of May 5, 2004.

Canada—Application No. 02–2985, filed Jan. 28, 2002, and Canadian Examination dated Apr., 2004; application still pending.

Fisher 2004 and Fisher USA 2004 catalogues offering 'Fiscor Electric' as novelty item (with shipment of plant material beginning in or after May 1, 2004).

* cited by examiner

*Primary Examiner*—Anne Marie Grunberg
*Assistant Examiner*—June Hwu
(74) *Attorney, Agent, or Firm*—Foley & Lardner LLP

(57) ABSTRACT

A new and distinct Poinsettia plant named 'Fiscor Electric' particularly described by the combined features of brilliant, orange-red bract color; medium sized inflorescence, ovate bracts; uniform dark-green foliage, ovate leaves with moderate lobes; medium sized, wide and rounded plant habit; and medium flowering response.

1 Drawing Sheet

Latin name of the genus and species of the plant claimed: *Euphorbia pulcherrima.*
Variety denomination: Fiscor Electric.

BACKGROUND OF THE INVENTION

The present invention relates to a new and distinct cultivar of Poinsettia plant botanically known as *Euphorbia pulcherrima* and hereinafter referred to by the variety denomination 'Fiscor Electric'.

'Fiscor Electric' was discovered by the inventor, Dirk Krüger, from a naturally occurring whole plant mutation of Poinsettia plant named 'Fiscor' (U.S. Plant Pat. No. 9,364). 'Fiscor' is characterized by deep red colored bracts, dark-green foliage with moderate lobes, and wide, medium sized plant habit.

In November 2001, a plant having several orange inflorescences was discovered among a crop of potted flowering plants of the parent variety 'Fiscor' in a greenhouse in Gönnebek, Germany. In December 2001, the plant was taken to Hillscheid, Germany, where the plant was left to develop vegetative shoots, which were cut for propagation in the spring of 2002.

Asexual reproduction of 'Fiscor Electric' was performed by vegetative terminal cuttings. Asexual reproduction of 'Fiscor Electric' was first performed in March of 2002 in Hillscheid, Germany. Horticultural examination of the plants grown thereof starting in the late summer of 2002 and continuing through 2003, has demonstrated that the combination of characteristics as herein disclosed for 'Fiscor Electric' are firmly fixed and retained through successive generations of asexual reproduction. The new cultivar reproduces true to type.

BRIEF SUMMARY OF THE INVENTION

The following traits have been repeatedly observed and are determined to be basic characteristics of 'Fiscor Electric', which in combination distinguish this Poinsettia as a new and distinct cultivar:

1. brilliant, orange-red bract color;
2. medium sized bracts, in a tight and flat, rosette-like arrangement;
3. uniform dark-green foliage with weak to moderate lobes;
4. about medium sized, wide, rounded plant habit; and
5. medium flowering response.

'Fiscor Electric' has not been observed under all possible environmental conditions. The phenotype may vary significantly with variations in environment such as temperature, light intensity, and day-length.

Of the many commercial cultivars known to the inventor, the most similar in comparison to 'Fiscor Electric' are the parental cultivar 'Fiscor' and the related variety 'Fiscor Fire', U.S. Plant Pat. No. 12,992. In comparison to 'Fiscor' and 'Fiscor Fire', 'Fiscor Electric' has a more brilliant and more orange hue of bract color. With reference to begin of flowering, the finishing time for plants of 'Fiscor Electric' corresponds that of 'Fiscor', while 'Fiscor Fire' is slightly earlier.

Furthermore, the reddish color of stems and pedicels is somewhat lighter for 'Fiscor Electric' than with 'Fiscor' and 'Fiscor Fire'.

BRIEF DESCRIPTION OF THE DRAWINGS

The accompanying color photographic drawing shows typical inflorescence and foliage of 'Fiscor Electric', with colors being as true as possible with illustrations of this type. The photograph shows a mature potted plant of 'Fiscor Electric' in its entirety featuring the brilliant, orange-red bract color and dark-green foliage.

DETAILED BOTANICAL DESCRIPTION

The following observations, measurements and comparisons describe plants grown in Langley, British Columbia, Canada, and in Hillscheid, Germany in the fall of 2002, under greenhouse conditions which approximate those generally used in commercial practice. Rooted cuttings were planted into 14 cm pots on July 17, and were pinched on August 1, leaving 7 to 8 leaves. Initially, the temperature was between a minimum of 19° C. and 24.5° C. maximum (ventilation temperature), and lower beginning October 1, with a minimum of 16° C. to 23° C. The plants initiated flowers under short-day conditions under natural short-day conditions in fall, no black cloth was applied.

Observations and measurements were mainly taken in mid December, when the plants were in full flower and about 20 weeks old. In the following description color references are made to The Royal Horticultural Society Colour Chart (R.H.S.). The color values were determined indoors in a North light.

Plant:

*Form.*—Shrub, self-branching.

Growth habit: About medium sized, pinched plants are bushy and round in shape.

Height (above soil line): 26.5 cm.

Width: 46.5 cm.

Average number of branches: 8.5.

Length of branches: 20–22 cm.

Diameter of branches: 5–6 mm.

Average number of inflorescence: 7.1.

Stem color: Lower part light green, RHS 144 B, upper parts of stems are weakly reddish infused, the resulting color is approximately RHS 181 C.

Internode length: About 20 mm.

Rooting: Medium, sufficiently rooted for transplanting after about 20–24 days in a greenhouse at a temperature of 22–24° C.

Blooming habit: Begin under natural short day conditions in fall: botanically (cyathia open): in early December, commercially (bracts colored, marketable): around December 1.

Flowering response time: About 9.5 weeks.

Foliage:

Shape: Broad elliptical to ovate, most often with rounded or obtuse base, with weak to medium lobes, acuminate tip, entire margin.

Texture: Upper surface: smooth and flat, only weakly veined, color of veins: mainly light green, RHS 145 B, at the base pink, RHS 179 B.

Lower surface: Flat and smooth, except for the slightly protruding midrib and finer side veins in a pinnate pattern, the vein color is near RHS 179 D.

Leaf blade size: Length: 14 cm; width 10.25 cm.

Petiole: Length: 6.5 to 7.5 cm, diameter 0.3 cm.

Quantity: About 50–55 leaves per plant.

Color: Generally dark green, uniform.

Mature foliage: Upper surface, RHS 139 A; under surface, RHS 139 B.

New foliage: Upper side: RHS 143 A; under side RHS 137 D.

Leaf petiole: Upper side: reddish-brown, RHS 181 A; lower side: RHS 176 D.

Aspect: Petioles are mostly horizontally directed, while the leaf blades slant downwards.

Flowering description: Whole inflorescence with surrounding bracts: about medium sized, star-shaped, with the bracts horizontally directed in a tight, overlapping arrangement.

Diameter: About 23–25 cm.

Height of inflorescence: About 20–25 mm, which is relatively flat.

Number of bracts per inflorescence: 10–13 (with a size over 2 cm).

Keeping quality: Good lasting quality will be maintained for about 4 weeks, no dropping of bracts.

Bracts:

Shape: Ovate, with rounded bases, weak lobes, and acuminate tips; bract blade is flat, with entire margin.

Size of the largest fully colored bract: 12.5 cm long, 7.8 cm wide.

Texture: Smooth, very little or no rugosity.

Vein color: Upper side corresponds closely to bract color; lower side pale orange to pale pink, near RHS 31 D to RHS 37 C.

Color: Generally deep orange-red, uniform; upper surface RHS 43 A; lower surface RHS 43 B.

Petiole: 12–15 mm long, color: upper side deep red, RHS 44 A, lower side from pale brown, RHS 170 D, to pale green, RHS 145 B.

Cyme: 18–22 mm in diameter, approximately 10 cyathia borne in a tight cluster.

Cyathium: Ovate, about 5–6 mm in diameter, medium to light green colored, RHS 143 B, top red, RHS 46 B; total length (with peduncle and female flower): 18–20 mm.

Peduncle: Color: Light green, RHS 143 C, 1–2 mm long, 3 mm in diameter, smooth, glabrous texture, average strength.

Nectar cups: Usually one or two per cyathium, 5 mm wide (1 honey-cup), 3–4 mm wide (2 honey-cups), brilliant yellow, RHS 12 A, to occasionally orange, RHS 25 A, no reddish coloring at the margin.

Reproductive organs:

*Stamens.*—About 5–15 in a cluster, filaments 3 mm, red RHS 46 B; moderate pollen, yellow, RHS 12 A.

*Anthers.*—Arrangement and shape: 2 round parts (thecae) side by side at the upper end of the filaments, each part under 1 mm in diameter, red color, RHS 46B (before shedding of pollen).

*Pistil.*—One per cyathium, pistil length (mature, before pollination) about 8 mm, style color, red, RHS 46B (lobes) to RHS 46C (base), stigma color, red RHS 45 B, stigma trifurcate, 6-lobed.

*Ovaries.*—Light to medium green, RHS 143 C, initially obovate, later triangular, diameter 3–4 mm, 5–6 mm long, 3 ovules.

*Fruit/seed set.*—No seed set observed.

Disease/pest resistance/susceptibility: No observations made.

I claim:

1. A new and distinct Poinsettia plant named 'Fiscor Electric' as described and illustrated herein.

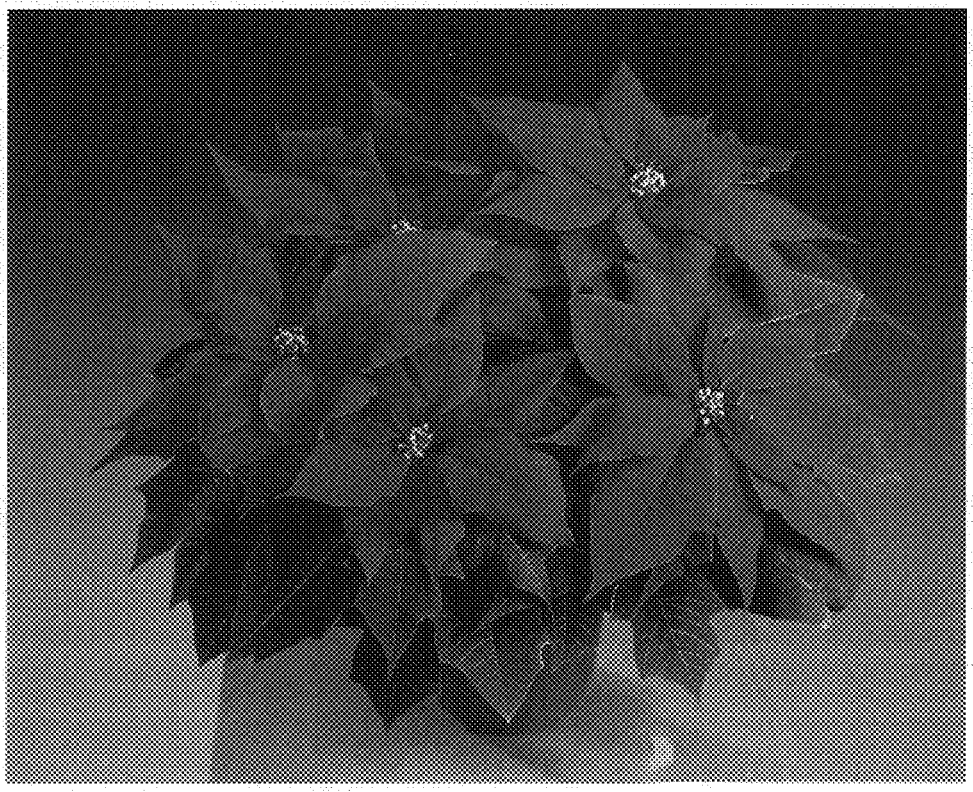

* * * * *